United States Patent [19]
Balestracci

[11] Patent Number: 6,030,367
[45] Date of Patent: Feb. 29, 2000

[54] PLUNGER ROD

[75] Inventor: Ernest Balestracci, Iselin, N.J.

[73] Assignee: Bracco Research, Princeton, N.J.

[21] Appl. No.: 09/273,901

[22] Filed: Mar. 22, 1999

[51] Int. Cl.[7] .................................................. A61M 5/315
[52] U.S. Cl. ........................... 604/218; 604/101; 604/232
[58] Field of Search .................................. 604/218, 232, 604/207, 187, 228, 181, 227

[56] References Cited

U.S. PATENT DOCUMENTS

| | | | |
|---|---|---|---|
| D. 403,762 | 1/1999 | Gabbard et al. | D24/113 |
| 4,543,093 | 9/1985 | Christinger | 604/228 |
| 5,411,488 | 5/1995 | Pagay et al. | 604/218 |
| 5,700,247 | 12/1997 | Grimard et al. | 604/220 |
| 5,860,961 | 1/1999 | Gettig | 604/199 |

FOREIGN PATENT DOCUMENTS

| | | | |
|---|---|---|---|
| WO 91/00114 | 1/1991 | WIPO | 604/218 |
| WO 93/09827 | 5/1993 | WIPO | 604/229 |

*Primary Examiner*—Wynn Wood Coggins
*Assistant Examiner*—J Maynard
*Attorney, Agent, or Firm*—Imre Balogh

[57] ABSTRACT

Dimensionally stable plunger rod for use with a plunger in a cartridge or syringe barrel for manual or power-assisted withdrawing of fluid from a site or expelling fluid from the cartridge or syringe barrel having:

- a plunger rod body with distal end proximal ends;
- an end disc at the distal end;
- a threaded member integral with the end disc designed to engage a plunger;
- a thumb rest at the proximal end;
- a reinforcing disc at about the longitudinal mid point of the plunger body;
- a first pair or rectangular radially extending vanes connecting the end and reinforcing discs;
- a second pair or rectangular radially extending vanes connecting the reinforcing disc and the thumb rest;
- a first pair of triangular radially extending vanes connecting the end disc and the reinforcing disc; and
- a second pair of triangular radially extending vanes connecting the reinforcing disc and the thumb rest.

10 Claims, 5 Drawing Sheets

FIG. 1 - PRIOR ART
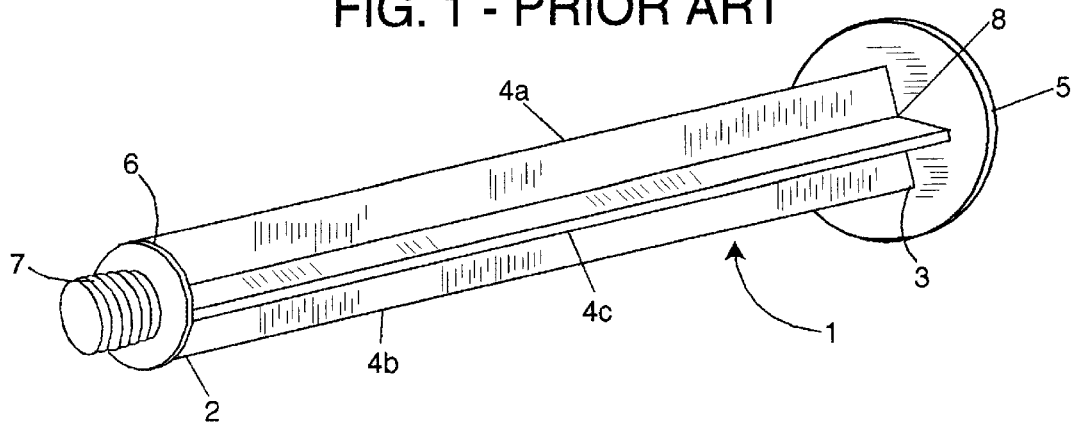
FIG. 2 - PRIOR ART
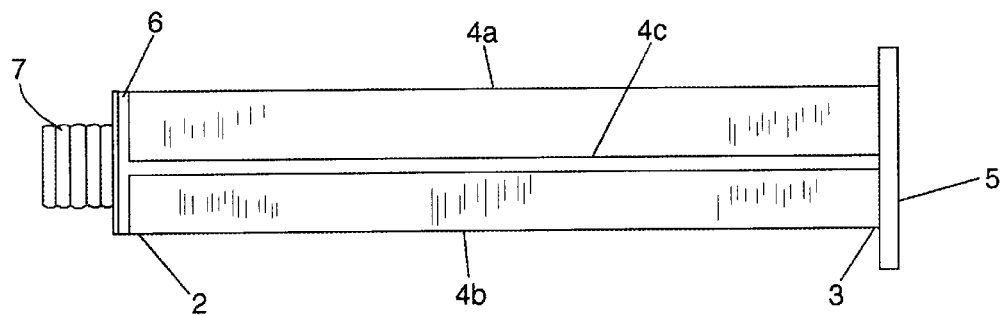
FIG. 3 - PRIOR ART
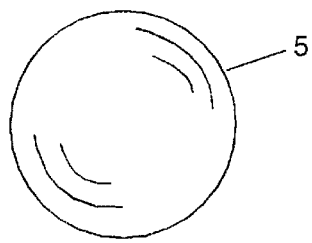
FIG. 4 - PRIOR ART
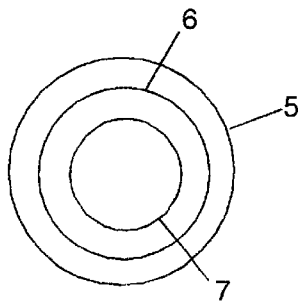

PLUNGER ROD

BACKGROUND OF THE INVENTION

1. Field of the Invention

The present invention relates to a plunger rod for use in a syringe or cartridge barrel having a plunger and containing a parenteral solution therein, or in a syringe or cartridge which are empty and are to be filled with a parenteral solution by the user at the time of administration.

The present invention also relates to a plunger rod for use in a syringe or cartridge containing a parenteral solution therein intended to be dispensed from a power injector.

2. Reported Developments

Syringes and cartridges made of glass or polymeric materials for dispensing parenteral solutions or withdrawing biological fluids from a patient are well known in the prior art. They comprise a cylindrical barrel with a tapered end at one end to which a needle or luer connector can be attached, and an open end which is stoppered by a plunger of a resilient thermoplastic or elastomeric material. The plunger serves the function of a stopper, when the barrel is filled with a fluid, or as a slidable member to expel the fluid from the barrel or withdraw a biological fluid from a patient or another source.

In order to expel fluid from the barrel or withdraw fluid into the barrel, the plunger is moved toward the distal end or the proximal end of the barrel by a plunger rod which is attachable to the plunger typically by screw threads. The user exerts a force, manually or by the use of a power injector, on the plunger rod to push and pull the plunger in the barrel. While the plunger rod does not contact the fluid in the barrel, it provides a very important function: it causes the plunger to move in an axial direction back and forth in the barrel when an external force is applied thereon.

The force applied to the plunger by the plunger rod should be perpendicular to the plunger so that the force exerted on the wall of the barrel by the plunger is uniform around the 360° of its cylindrical configuration. To wit, the direction of movement of the plunger rod should always be perpendicular to the surface of the plunger. When the plunger rod flexes in the barrel, the direction of force on the plunger will not be uniform resulting in pressure points at certain areas of contact between the plunger and the inside wall of the barrel and, conversely, inadequate pressure points at other parts of the interface between the plunger and the inside wall of the barrel. Such pressure differences tend to allow leakage and difficulty in moving the plunger at an even rate in the barrel.

Recognizing the importance of dimensional stability, the prior art has incorporated various stability enhancing means into plunger rods which include the following.

The assembly disclosed in U.S. Pat. No. 4,543,093 has a plunger rod the central portion of which is almost as large as the inside diameter of the syringe barrel so that it will assist in keeping the plunger rod assembly concentrically aligned within the syringe barrel.

WO93/09827 discloses a shank having a plurality of longitudinal and radially extending vanes. In one preferred embodiment the shank is provided with four vanes in an "X" pattern while in another preferred embodiment the shank is provided with three vanes forming a "Y" pattern.

U.S. Pat. Nos. 5,700,247 and 5,860,961 disclose plunger rods having a plurality of vanes or support ribs.

A common feature of these plunger rods is a shank extending between the distal and proximal ends of the plunger rods having vanes or support ribs thereon. The vanes or support ribs are identical with one another running longitudinally on the shank and extending radially therefrom.

I have now discovered a strong, dimensionally stable plunger rod which is of novel configuration and is useful in combination with plungers intended for use in syringe or cartridge barrels for manual or power injections.

SUMMARY OF THE INVENTION

The present invention provides a strong, dimensionally stable plunger rod designed for use in a cartridge or syringe barrel having a plunger therein for withdrawing fluid from a site or expelling fluid from the barrel of a cartridge or syringe. The plunger rod may be used in manual or power-assisted fluid withdrawal or delivery systems.

The plunger rod of the present invention has two embodiments, both of which are characterized by the presence of a reinforcing disc at about the longitudinal mid point of the plunger rod.

One embodiment of the plunger rod having a distal end and a proximal end comprises:

an end disc at the distal end;

a threaded member integral with the end disc designed to engage a plunger;

a thumb rest at the proximal end for facilitating exertion of external pressure on the plunger rod;

a reinforcing disc at about the longitudinal mid point of the plunger rod;

a first pair of rectangular radially extending vanes connecting the end disc and the reinforcing disc;

a second pair of rectangular radially extending vanes connecting the reinforcing disc and the thumb rest;

a first pair of isosceles triangular radially extending vanes connecting the end disc and the reinforcing disc, wherein the smallest angle of the isosceles triangular vanes point toward the reinforcing disc; and a second pair of isosceles triangular radially extending vanes connecting the reinforcing disc and the thumb rest, wherein the smallest angle of the isosceles triangular vanes point toward the reinforcing disc;

wherein:

said first pair of said rectangular radially extending vanes and said first pair of said isosceles triangular radially extending vanes are integral with each other and with said end disc and said reinforcing disc; and said second pair of said rectangular radially extending vanes and said second pair of said isosceles triangular radially extending vanes are integral with each other and with said reinforcing disc and said thumb rest.

The other embodiment of the plunger rod having a distal end and a proximal end comprises:

an end disc at the distal end;

a threaded member integral with the end disc designed to engage a plunger;

a thumb rest at the proximal end for facilitating exertion of external pressure on the plunger rod;

a reinforcing disc at about the longitudinal mid point of the plunger rod;

a first pair of rectangular radially extending vanes connecting the end disc and the reinforcing disc;

a second pair of rectangular radially extending vanes connecting the reinforcing disc and the thumb rest;

a first pair of isosceles triangular radially extending vanes connecting the end disc and the reinforcing disc wherein the smallest angle of the isosceles triangular vanes point toward the end disc;

a second pair of isosceles triangular radially extending vanes connecting the reinforcing disc and the thumb rest, wherein the smallest angle of the isosceles triangular vanes point toward the thumb rest;

wherein;

said first pair of said rectangular radially extending vanes and said first pair of said isosceles triangular radially extending vanes are integral with each other and with said end disc and said reinforcing disc; and said second pair of said rectangular radially extending vanes and said second pair of said isosceles triangular radially extending vanes are integral with each other and with said reinforcing disc and said thumb rest.

BRIEF DESCRIPTION OF THE DRAWINGS

FIG. 1 is a perspective view of a typical prior art plunger rod;

FIG. 2 is a side-elevational view thereof;

FIG. 3 is a bottom plan view thereof;

FIG. 4 is a top plan view thereof;

FIG. 6 is a side-elevational view of the plunger rod shown in

FIG. 5;

DETAILED DESCRIPTION OF THE INVENTION

Figure 5:
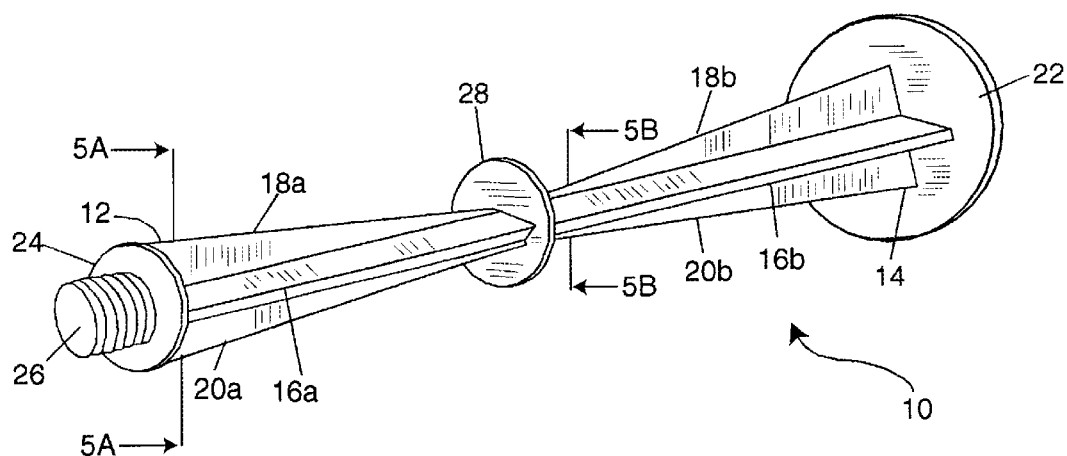
FIG. 5 is a perspective view of one embodiment of the plunger rod of the present invention.

Referring to FIGS. 1–4, a typical prior art plunger rod is shown in perspective, side-elevational, bottom plan and top plan views. Plunger rod 1 having a distal end 2 and a proximal end 3 comprises: longitudinal and radially extending vanes 4a, 4b, 4c and 4d (4d is hidden in the perspective view); a thumb rest 5 at the proximal end 3 and a disc 6 at the distal end 2 of the plunger rod; and a screw threaded member 7 extending from disc 6 designed to engage a plunger. As shown, vanes 4a, 4b, 4c and 4d are equivalent to one another extending from thumb rest 5 to disc 6. These vanes meeting at the center 8 of the plunger rod are of rectangular configuration.

Referring now to one embodiment of the present invention shown in FIGS. 5–9, the configuration of the plunger rod is atypical compared to the plunger rod shown in FIGS. 1–4. Plunger rod 10 having a distal end 12 and a proximal end 14 comprises:

longitudinal radially extending vanes 16a and 16b (16c and 16d are hidden in FIG. 5) having a rectangular configuration; longitudinal radially extending vanes 18a, 18b, 20a and 20b having a triangular configuration; a thumb rest 22 at the proximal end of the plunger rod 10; a disc 24 at the distal end 12 of the plunge rod; a screw threaded member 26 extending from disc 24 designed to engage a plunger; and a central disc 28 located at about the mid point between thumb rest 22 and disc 24.

As shown in the drawings central disc 28 supports the rectangular vanes and the triangular vanes and is integral therewith to provide dimensional stability to the plunger rod. Cross sectional view of FIG. 5A illustrates that at the proximal end 12 of the plunger rod the rectangular and triangular vanes are of about equal in size in the radial direction, however, while the rectangular vanes connecting to central disc 28 maintain their rectangular configuration, the triangular vanes diminish in size in the radial direction into central disc 28 and merge with both the rectangular vanes and the central disc. Cross-sectional view of the plunger rod in FIG. 5B shows that rectangular vane 16b is the same size as rectangular vane 16a shown in cross-sectional view in FIG. 5A, while triangular vane 18b diminishes to a small size and merges with rectangular vane 16b.

Figure 5A:
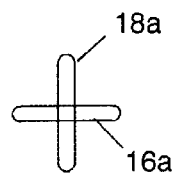
FIG. 5A is a cross-sectional view of the plunger rod taken along the line 5A—5A of FIG. 5.
Figure 5B:
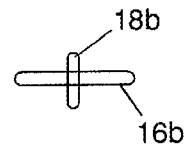
FIG. 5B is another cross-sectional view of the plunger rod taken along the line 5B—5B of FIG. 5.
Figure 6:
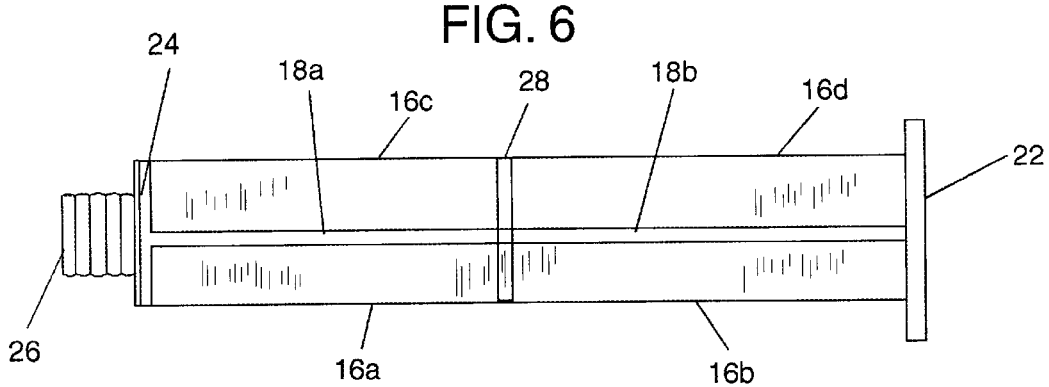

FIG. 6 shows the plunger rod of FIG. 5 in a side-elevational view where triangular vanes 18a and 18b are at the center of the Fig., and rectangular vanes 16a, 16b, 16c and 16d are at the sides of the Fig.

Figure 7:
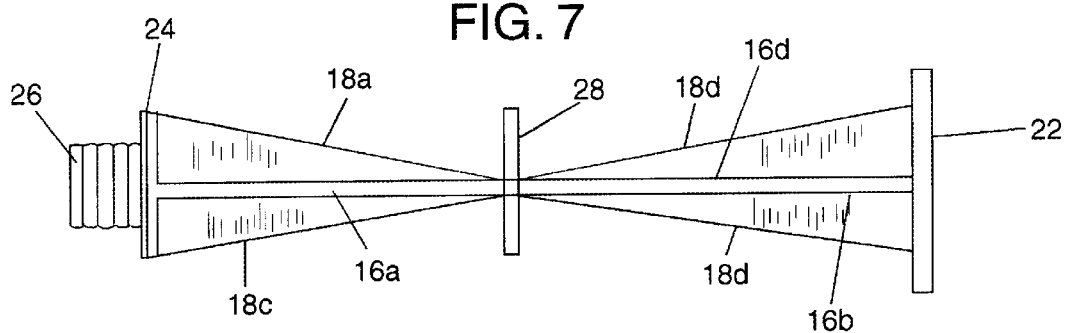
FIG. 7 is another side-elevational view of the plunger rod shown in FIG. 5 rotated 90° from that shown in FIG. 6.

FIG. 7 is another side-elevational view of the plunger rod of FIG. 5 rotated 90° from that shown in FIG. 6. Here, triangular vanes 18a, 18b, 18c and 18d are at the sides of the Fig. and rectangular vanes 16a and 16b are at the center thereof.

Figure 8:
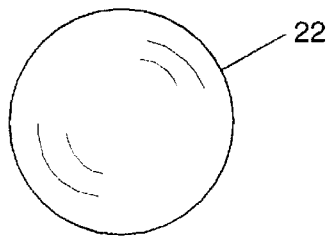
FIG. 8 is a bottom plan view of the plunger rod shown in FIG. 5.
Figure 9:
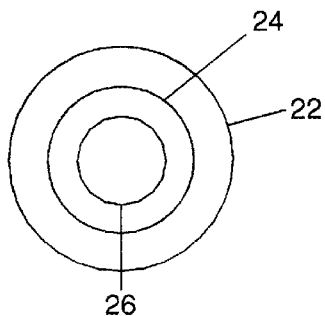
FIG. 9 is a top plan view of the plunger rod shown in FIG. 5.

FIGS. 8 and 9 show respectively the bottom and top plan views of the plunger rod.

FIGS. 10–14 show another embodiment of the present invention wherein the orientation of the triangular vanes are reversed to that shown in FIGS. 5–9.

Plunger rod 30 having a distal end 32 and a proximal end 34 comprises:

longitudinal radially extending vanes 36a and 36b (36c and 36d are hidden in FIG. 10) having a rectangular configuration;

longitudinal radially extending vanes 38a, 38b, 38c and 38d having triangular configuration; thumb rest 40 at the proximal end 34 of the plunger rod 30;

a disc 42 at the distal end 32 of the plunger rod;

a screw threaded member 44 extending from the disc 42 designed to engage a plunger;

and a central disc 46 located at about the mid point between thumb rest 40 and disc 42.

Figure 10:
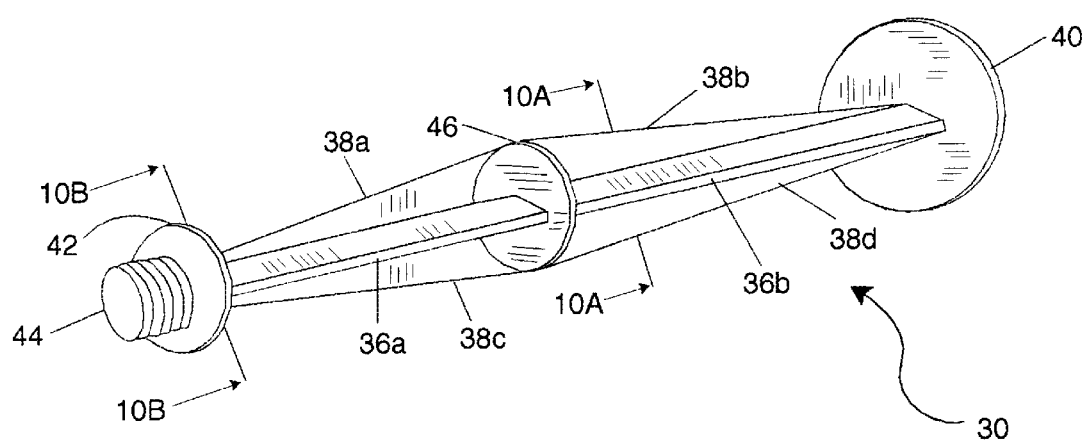
FIG. 10 is a perspective view of another embodiment of the plunger rod of the present invention.
Figure 10A:
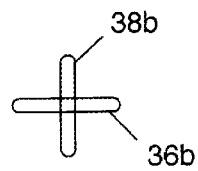
FIG. 10A is a cross-sectional view of the plunger rod taken along the line 10A—10A of FIG. 10.
Figure 10B:
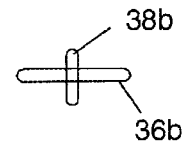
FIG. 10B is a cross-sectional view of the plunger rod taken along the line 10B—10B of FIG. 10.

Central disc 46 supports the rectangular vanes and the triangular vanes and is integral therewith to provide dimensional stability to the plunger rod. Cross sectional view FIG. 10A, taken along the line 10A—10A of FIG. 10 illustrates that at about the mid point of the plunger rod the rectangular and triangular vanes are about equal in size in the radial direction, however, while the rectangular vanes connecting to the central disc 46, disc 42 and thumb rest 40 maintain their rectangular configuration, the triangular vanes diminish in size in the radial direction as it approaches disc 42 and thumb rest 40. As shown, the triangular vanes merge with the rectangular vanes at disc 42 and thumb rest 40. Cross-sectional view of the plunge rod in FIG. 10B, taken along the line 10B—10B of FIG. 10, shows that triangular vanes 38a, 38b, 38c and 38d diminish to a small size and merge with rectangular vanes 36a and 36b at disc 42 and thumb rest 40.

Figure 11:
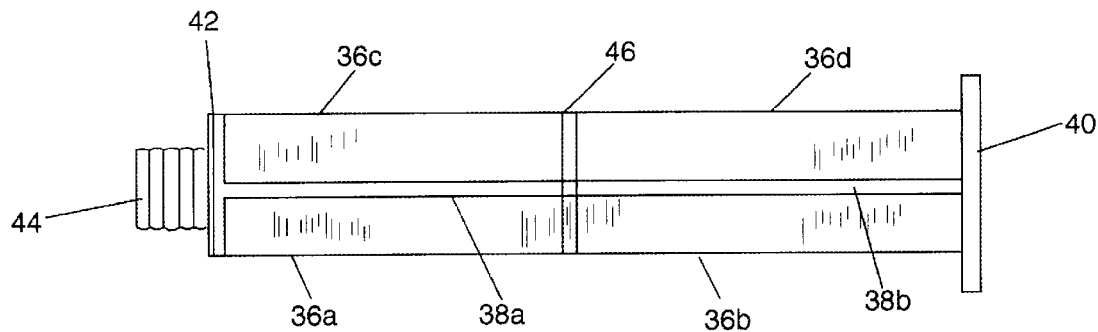
FIG. 11 is a side-elevational view of the plunger rod shown in FIG. 10.

FIG. 11 shows the plunger rod of FIG. 10 in a side-elevational view where triangular vanes 38a and 38b are at the center of the Fig., and rectangular vanes 36a, 36b, 36c and 36d are at the sides of the Fig.

Figure 12:
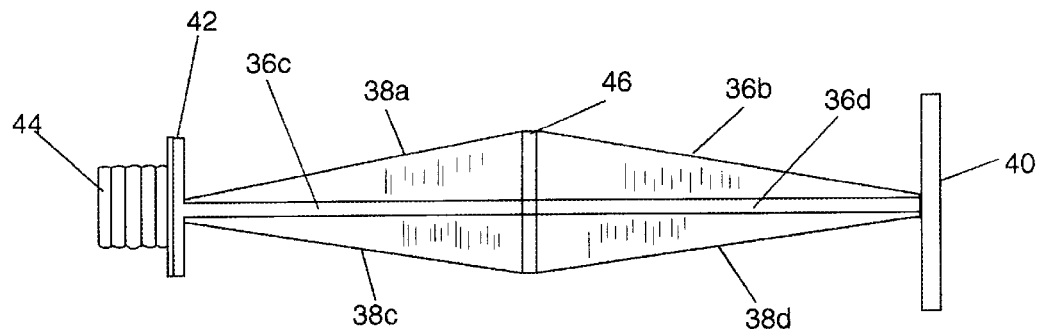
FIG. 12 is another side-elevational view of the plunger rod shown in FIG. 10 rotated 90° from that shown in FIG. 11.

FIG. 12 is another side elevational view of the plunger rod of FIG. 10 rotated 90° from that shown in FIG. 11. The triangular vanes 38a, 38b, 38c, and 38d are at the sides of the Fig. and rectangular vanes 36c and 36d are at the center thereof.

Figure 13:
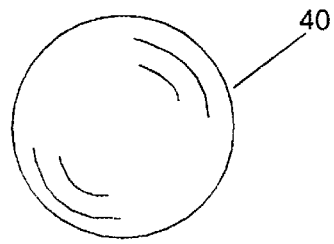
FIG. 13 is a bottom plan view of the plunger rod shown in FIG. 10.
Figure 14:
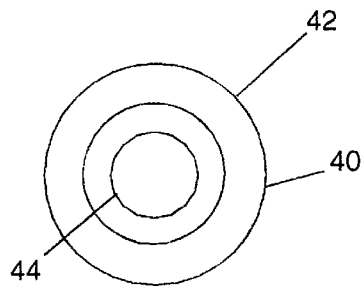
FIG. 14 is a top plan view of the plunger rod shown in FIG. 10.

FIGS. 13 and 14 show respectively the bottom and top plan views of the plunger rod.

The plunger rod of the present is made by injection molding well-known in the art using thermoplastic materials. Polypropylene, polyethylene and blend thereof are preferred for providing strength to the plunger rod. However, other polymers, such as polystyrenes, polyesters and polycarbonates may also be used.

Various modifications of the present invention will become apparent to those skilled in the art. This invention is intended to include such modifications to be limited only by the scope of the claims.

What is claimed is:

1. A dimensionally stable plunger rod for use with a plunger in a cartridge or syringe barrel for manual or power-assisted withdrawing of fluid from a site or expelling fluid from the cartridge or syringe barrel comprising:

a plunger rod body having a distal end and a proximal end;

an end disc at said distal end;

a threaded member integral with said end disc adapted to engage said plunger;

a thumb rest at said proximal end for facilitating exertion of an external pressure on said plunger rod body;

a reinforcing disc at about the longitudinal mid point of said plunger rod body;

a first pair of rectangular radially extending vanes connecting said end disc and said reinforcing disc;

a second pair of rectangular radially extending vanes connecting said reinforcing disc and said thumb rest;

a first pair of isosceles triangular radially extending vanes connecting said end disc and said reinforcing disc, wherein the smallest angle of said isosceles triangular vanes point toward said reinforcing disc; and a second pair of isosceles triangular radially extending vanes connecting said reinforcing disc and said thumb rest, wherein the smallest angle of said isosceles triangular vanes point toward said reinforcing disc;

wherein:

said first pair of rectangular radially extending vanes and said first pair of isosceles triangular radially extending vanes are integral with each other and with said end disc and said reinforcing disc; and said second pair of rectangular radially extending vanes and said second pair of isosceles triangular radially extending vanes are integral with each other and with said reinforcing disc and said thumb rest.

2. The dimensionally stable plunger rod of claim 1 made of a thermoplastic polymer.

3. The dimensionally stable plunger rod of claim 1 made of polypropylene, polyethylene and blends thereof.

4. The dimensionally stable plunger rod of claim 1 made of a polymeric material selected from the group consisting of polystyrenes, polyesters and polycarbonates.

5. The dimensionally stable plunger rod of claim 1 made by injection molding.

6. A dimensionally stable plunger rod for use with a plunger in a cartridge or syringe barrel for manual or power-assisted withdrawing of fluid from a site or expelling fluid from the cartridge or syringe barrel comprising:

a plunger rod body having a distal end and a proximal end;

an end disc at the distal end;

a threaded member integral with said end disc adapted to engage said plunger;

a thumb rest at the distal end for facilitating exertion of an external force on said plunger rod body;

a reinforcing disc at about the longitudinal mid point of said plunger rod body;

a first pair of rectangular radially extending vanes connecting said end disc and said reinforcing disc;

a second pair of rectangular radially extending vanes connecting said reinforcing disc and said thumb rest;

a first pair of isosceles triangular radially extending vanes connecting said end disc and said reinforcing disc, wherein the smallest angle of said isosceles triangular vanes point toward said end disc;

a second pair of isosceles triangular radially extending vanes connecting said reinforcing disc and said thumb rest, wherein the smallest angle of said isosceles triangular vanes point toward said thumb rest;

wherein:

said first pair of rectangular radially extending vanes and said first pair of isosceles triangular radially extending vanes are integral with each other and with said end disc and said reinforcing disc; and said second pair of rectangular radially extending vanes and said second pair of isosceles triangular radially extending vanes are integral with each other and with said reinforcing disc and said thumb rest.

7. The dimensionally stable plunger rod of claim 6 made of a thermoplastic polymer.

8. The dimensionally stable plunger rod of claim 6 made of polypropylene, polyethylene and blends thereof.

9. The dimensionally stable plunger rod of claim 6 made of a polymeric material selected from the group consisting of polystyrenes, polyesters and polycarbonates.

10. The dimensionally stable plunger rod of claim 6 made by injection molding.

* * * * *